US008419713B1

(12) United States Patent
Solomon et al.

(10) Patent No.: US 8,419,713 B1
(45) Date of Patent: Apr. 16, 2013

(54) CARRIER ASSEMBLY WITH CAPS FOR MEDICAL CONNECTORS

(75) Inventors: Donald D. Solomon, North Salt Lake, UT (US); James Paul Kennedy, Salt Lake City, UT (US)

(73) Assignee: The University of Utah Research Foundation, Salt Lake City, UT (US)

( * ) Notice: Subject to any disclaimer, the term of this patent is extended or adjusted under 35 U.S.C. 154(b) by 0 days.

(21) Appl. No.: 13/564,122

(22) Filed: Aug. 1, 2012

(51) Int. Cl.
*A61M 39/00* (2006.01)

(52) U.S. Cl.
USPC ........................................ 604/533; 15/104.93

(58) Field of Classification Search .................. 604/533, 604/256, 905; 422/28, 292; 15/104.92, 104.93, 15/210.1; 215/204; 220/23.83, 23.87, 23.88, 220/23.89
See application file for complete search history.

(56) References Cited

U.S. PATENT DOCUMENTS

| 1,744,026 | A | | 1/1930 | Baltzley | |
|---|---|---|---|---|---|
| 3,431,548 | A | | 3/1969 | Busler | |
| 4,572,373 | A | | 2/1986 | Johansson | 206/515 |
| 4,667,837 | A | * | 5/1987 | Vitello et al. | 215/228 |
| 5,445,270 | A | | 8/1995 | Dratz | 206/443 |
| 5,702,017 | A | | 12/1997 | Goncalves | 220/23.4 |
| 6,523,686 | B1 | | 2/2003 | Bae | 206/315.9 |
| 7,762,988 | B1 | * | 7/2010 | Vitello | 604/111 |
| 7,780,794 | B2 | | 8/2010 | Rogers et al. | 134/6 |
| 2004/0195136 | A1 | | 10/2004 | Young et al. | 206/484 |
| 2007/0112333 | A1 | | 5/2007 | Hoang et al. | 604/533 |
| 2008/0019889 | A1 | | 1/2008 | Rogers et al. | 422/292 |
| 2010/0047123 | A1 | | 2/2010 | Solomon et al. | 422/28 |
| 2011/0054440 | A1 | * | 3/2011 | Lewis | 604/506 |
| 2011/0232020 | A1 | | 9/2011 | Rogers et al. | 15/246 |
| 2011/0277788 | A1 | | 11/2011 | Rogers et al. | 134/6 |
| 2012/0216359 | A1 | | 8/2012 | Rogers et al. | 15/104.93 |

* cited by examiner

*Primary Examiner* — Kevin C Sirmons
*Assistant Examiner* — Imani Hayman
(74) *Attorney, Agent, or Firm* — Sunstein Kann Murphy & Timbers LLP

(57) ABSTRACT

An assembly for mounting medical connector caps includes a carrier formed from a sheet of material and having an array of holes. The assembly also includes a plurality of medical connector caps. Each cap is inserted into one of the holes of the array. The assembly also includes a plurality of sealing tabs. A distinct sealing tab includes a cover portion that sealingly covers the openable end of a corresponding one of the caps and includes an overhang portion that overhangs the openable end thereof. The overhang portion is dimensioned to include a tether of sufficient length that a tip of the tether overlaps an adjacent portion of the carrier. The tip is affixed to the carrier, so that the corresponding one of the caps is tethered to the carrier by such sealing tab.

13 Claims, 5 Drawing Sheets

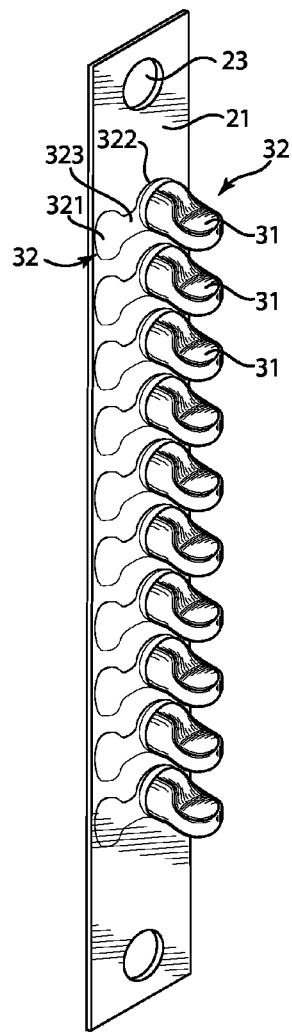
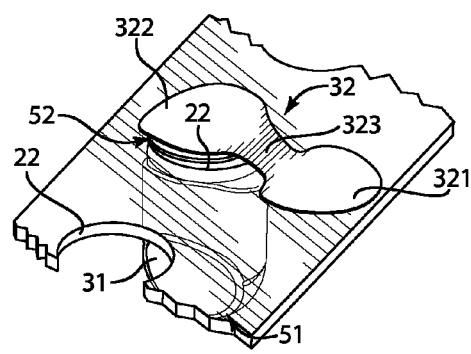
Fig. 4
Fig. 5

CARRIER ASSEMBLY WITH CAPS FOR MEDICAL CONNECTORS

TECHNICAL FIELD

The present invention relates to medical connector caps, and more particularly to assemblies of such caps that provide a seal over the openable end of such caps.

BACKGROUND ART

It is known in the prior art to provide a female medical connector cap with a seal over its openable end, so as to enable storage of the connector cap in a manner to prevent contamination of the interior of the cap. It is also known in the prior art to provide an assembly employing a sealing strip, composed of a foil-based material or foil-based composite, that seals the openable end of each of a series of female medical connector caps affixed to the sealing strip. Assemblies of this sort have a number of disadvantages, including a risk that, in dislodging a selected one of the caps from the sealing strip for use, another one of the caps might be partially or completely dislodged from the sealing strip and therefore suffer a risk of contamination. Moreover, in dislodging a cap from the strip, it is convenient to grab, with one hand, the strip near where the cap is attached and to grab, with the other hand, the cap near where it is attached to the strip; both hands are therefore near the opening of the cap as it becomes uncovered, and there is a risk that one or more fingers of the user will come into contact with the opening of the cap and introduce microorganisms into it, so as to defeat the purpose of the cap and the strip of protecting the medical connector from microorganisms.

SUMMARY OF THE EMBODIMENTS

In a first embodiment of the invention there is provided an assembly mounting medical connector caps for use. In this embodiment, the assembly includes a carrier formed from a sheet of material. The carrier has an array of holes. The assembly also includes a plurality of medical connector caps, each cap having (i) an openable end configured to cover a medical connector and (ii) a closed graspable end. Each cap is inserted into one of the holes of the array. The assembly also includes a plurality of sealing tabs. A distinct sealing tab includes a cover portion that sealingly covers the openable end of a corresponding one of the caps and includes an overhang portion that overhangs the openable end thereof. The overhang portion is dimensioned to include a tether of sufficient length that a tip of the tether overlaps an adjacent portion of the carrier. The tip is affixed to the carrier, so that the corresponding one of the caps is tethered to the carrier by such sealing tab. The assembly is configured so that a user can prepare a selected one of the caps for use by grasping its graspable end and both removing the selected cap from its corresponding hole and tearing away its openable end from the cover portion of the sealing tab, utilizing the tether to retain the sealing tab as affixed to the carrier.

In a related embodiment, the tether is configured so that when a user prepares the selected one of the caps for use, a user can choose to manipulate the cap in relation to the carrier so as to break the tether and remove the cap from its corresponding hole, while leaving the cover portion of the sealing tab to sealingly cover the openable end of the cap, so that a user may remove the cover portion at a desired time after removing the cap from its corresponding hole.

Optionally, each of the holes into which one of the caps is inserted is sized to secure such cap therein with a friction fit, so as to mechanically stabilize such cap in relation to the carrier.

Optionally, each of the caps includes a disinfectant disposed therein.

Optionally, the sheet of material is flexible.

In various further embodiments, the sheet of material is a polymeric film, such as a polyolefin. Optionally, the polyolefin is selected from the group consisting of polyethylene and polypropylene. Also optionally, the polyolefin is polyethylene.

Also further embodiments, the sealing tabs are made of metal foil. In other embodiments, the sealing tabs are made of a composite polymeric sheet with a metal foil layer.

BRIEF DESCRIPTION OF THE DRAWINGS

The foregoing features of embodiments will be more readily understood by reference to the following detailed description, taken with reference to the accompanying drawings, in which:

FIG. 4 is another perspective view of the assembly of FIG. 3, this time as seen from the upper side of the carrier;

FIG. 5 is a perspective view from the underside of the assembly of FIG. 3, providing detail with respect to a single connector cap of the assembly;

In FIG. 6, the user is seen to have grasped with one hand a graspable end of the connector cap while with another hand to have grasped the carrier;

In FIG. 7, the user has partially removed the cap from its corresponding hole in the carrier and caused some of the cover portion of the sealing tab to be removed from the openable end of the cap; and In FIG. 8, the user has complete removed the cap from its corresponding hole in the carrier and caused the cover portion of the sealing tab to be removed from the openable end of the cap.

DETAILED DESCRIPTION OF SPECIFIC EMBODIMENTS

Definitions. As used in this description and the accompanying claims, the following terms shall have the meanings indicated, unless the context otherwise requires:

A "medical connector cap" is a cap for a medical connector, such as (but not limited to) a luer connector. Consequently, a "female medical connector cap" is a cap for a female medical connector. A "male medical connector cap" is a cap for a male medical connector. The cap may, but need not necessarily, include a disinfectant. The cap may, but need not necessarily, be capable of cleaning or disinfecting the medical connector for which it is a cap.

The "openable end" of a medical connector cap is the end of the cap that is open to a cavity into which the medical connector is received. Typically, prior to use, the openable end of the medical connector cap is covered in one manner or another to prevent contamination of the interior of the cap, and for that reason we term this end as "openable" rather than "open".

The "graspable end" of a medical connector cap is the end of the cap that is grasped by the user in placing the cap on a medical connector and in removing the cap from the medical connector. We refer to the graspable end as "closed" because the cavity of the medical connector cannot be reached from the graspable end.

Figure 1:
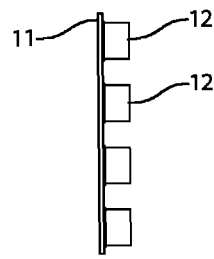
FIG. 1 is a side view of a prior art assembly of female medical connector caps affixed to a sealing tab.

FIG. 1 is a side view of a prior art assembly of female medical connector caps 12 affixed to a sealing tab 11. The sealing tab 11 is designed to provide a seal over the openable end of each of the female connector caps 12, and therefore must be made of a suitable material, such as metal foil or a composite plastic sheet with a foil layer as a barrier. Assemblies of this sort have a number of disadvantages, including a risk that, in dislodging one of the caps from the sealing tab for use, another one of the caps might be partially or completely dislodged from the sealing tab and therefore suffer a risk of contamination.

Figure 2:
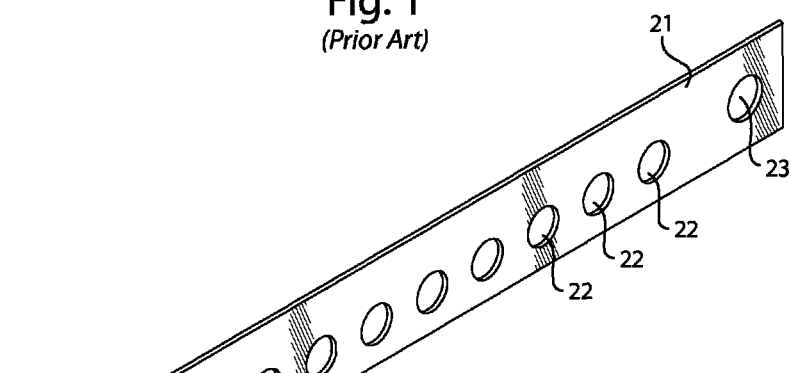
FIG. 2 is a perspective view of a carrier for use in connection with an embodiment of the present invention.

FIG. 2 is a perspective view of a carrier 21 for use in connection with an embodiment of the present invention. The carrier includes a sheet that may be made of any suitable material. Suitable materials may be polymeric or composite polymeric materials, such as a polyolefin, styrene, polyethylene terephthalate (PET, including Mylar), polyvinyl chloride (PVC), or polyurethane. Of the polyolefins, low or high density polyethylene may be suitable, as well as polypropylene. Although the sheet may desirably be flexible, in other applications, a rigid sheet may also be employed for the carrier.

The carrier 21 includes at least one mounting hole 23, located to facilitate mounting of the carrier at one end, and may optionally include a pair of mounting holes 23 at each end or any desired number of mounting holes. One of the mounting holes 23 may be used, for example, to hang the carrier on a hook or other member protruding from an IV pole. Alternatively, a pair of mounting holes 23 may be used simultaneously to mount the carrier 21 in an approximately horizontal orientation. The carrier 21 also includes an array of holes 22 for receiving therein a corresponding population of medical connector caps, in a manner discussed in further detail below.

Figure 3:
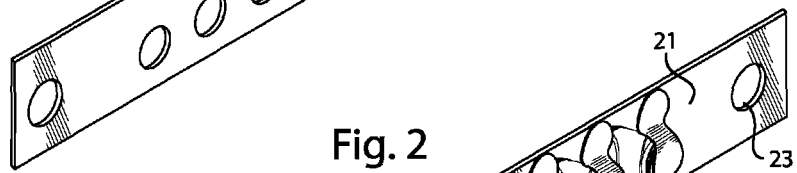
FIG. 3 is a perspective view of an assembly including the carrier of FIG. 2, as seen from the underside of the carrier, populated with medical connector caps, in accordance with an embodiment of the present invention.

FIG. 3 is a perspective view of an assembly including the carrier 21 of FIG. 2, as seen from the underside of the carrier, populated with medical connector caps 31, in accordance with an embodiment of the present invention. A medical connector cap 31 resides in each hole 22 in the array of holes in the carrier 21 depicted in FIG. 2. Each hole 22 is sized to secure its corresponding cap with a friction fit, so as to mechanically stabilize the cap in relation to the carrier. The carrier may be suitably populated with female medical connector caps. Alternatively, the carrier may be suitably populated with male medical connector caps. As yet another alternative, the carrier may be populated with a mixture of male and female medical connector caps. Because the dimensions of caps for male medical connectors are typically different from the dimensions of caps for female medical connectors, the size of the holes 22 will typically need to be sized according to specific medical connector cap intended to be resident therein. In an alternative embodiment, the holes 22 are configured to receive the medical connector caps without a friction fit.

In the embodiment of FIG. 3, each cap 31 has a separate sealing tab 32. The sealing tab 32 includes a cover portion 322, which sealingly covers the openable end of the cap 31.

The sealing tab also includes an overhang portion that overhangs the openable end of the cap 31. The overhang portion is dimensioned to include a tether 323 of sufficient length that a tip 321 of the tether overlaps an adjacent portion of the carrier 2. The tip 321 is affixed to the carrier 21, so that the corresponding cap 31 is tethered to the carrier 21 by the sealing tab 32. The sealing tab may be made of metal foil or it may be a composite polymeric sheet with a metal foil layer as a barrier. In the event a composite is used for the sealing tab, it is necessary only that the foil layer should exist over the openable end of the cap 31; no foil is needed on the tether 323 or the tip 321 of the tether, although optionally the entire tab may include the foil layer. The sealing tab 32 may be affixed to the openable end of the cap 31 and to the carrier 21 by glue, UV adhesive, mechanical means, or by thermal bonding.

FIG. 4 is another perspective view of the assembly of FIG. 3, this time as seen from the upper side of the carrier.

FIG. 5 is a perspective view from the underside of the assembly of FIG. 3, providing detail with respect to a single connector cap of the assembly.

Figure 6:
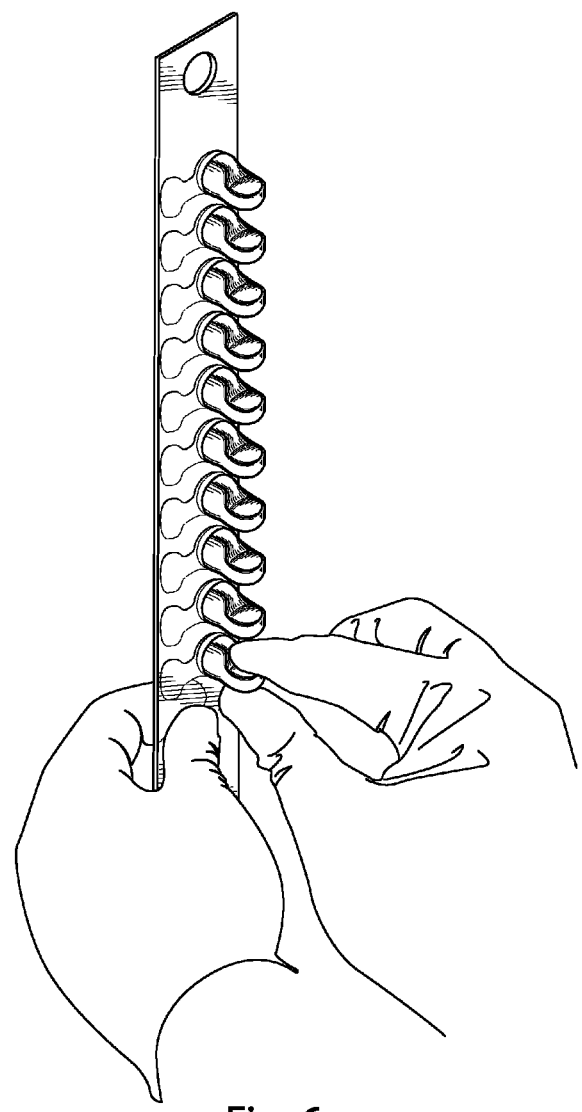
FIGS. 6-8 are a series of perspective views showing how the assembly can be used to prepare a medical connector cap for use.
Figure 7:
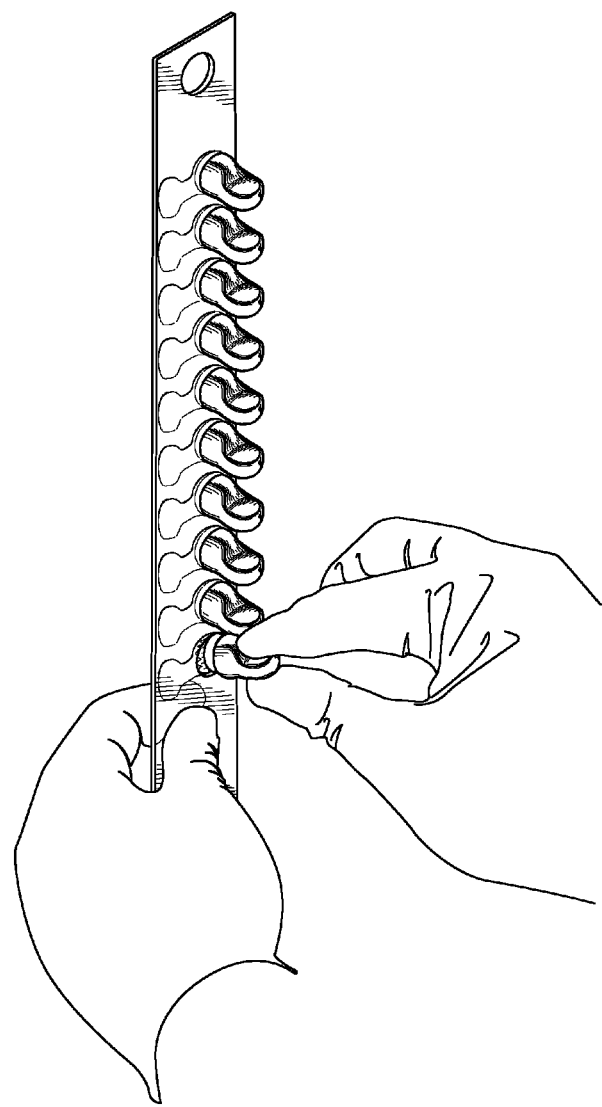
Figure 8:
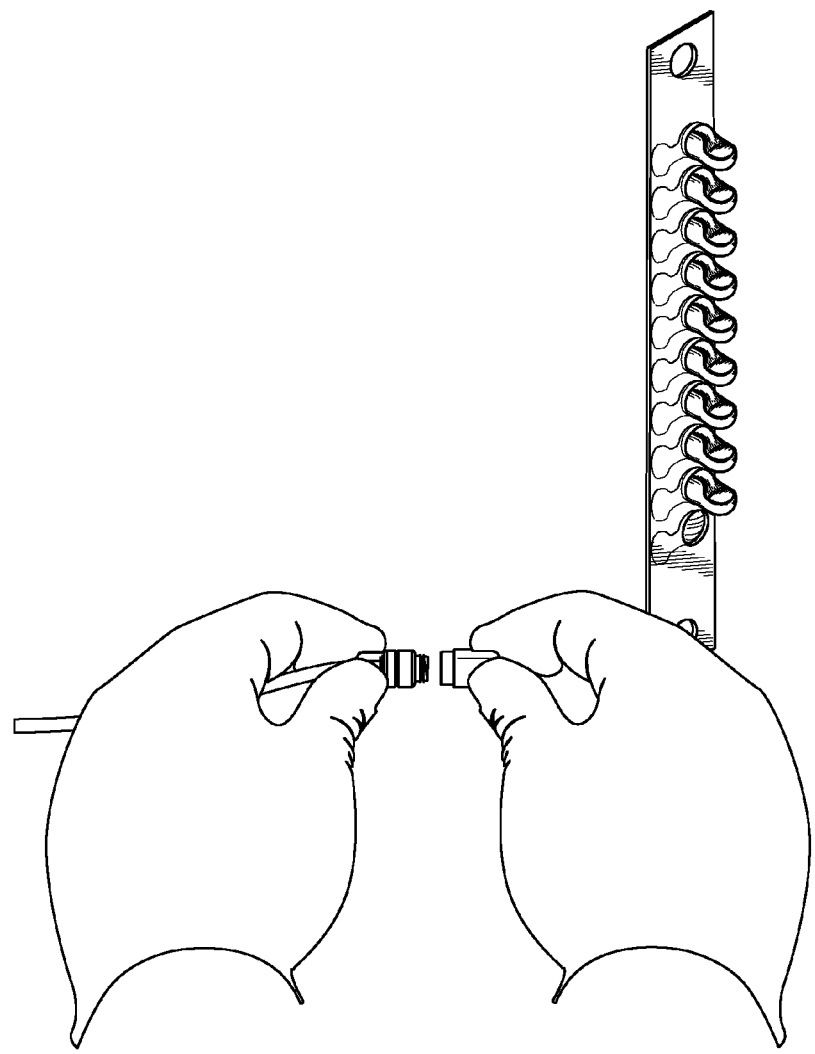

FIGS. 6-8 are a series of perspective views showing how the assembly can be used to prepare a medical connector cap for use. In FIG. 6, the user is seen to have grasped with one hand the graspable end of the connector cap while with another hand to have grasped the carrier.

In FIG. 7, the user has partially removed the cap from its corresponding hole 22 in the carrier 21 and caused some of the cover portion 322 of the sealing tab 32 to be removed from the openable end of the cap. The tether 323 and its tip 321 keep the sealing tab 32 affixed to the carrier 21.

In FIG. 8, the user has completely removed the cap from its corresponding hole in the carrier and caused the cover portion of the sealing tab to be removed from the openable end of the cap. The tether 323 and its tip 321 continue to keep the sealing tab 32 affixed to the carrier 21. In FIG. 8, the user is seen to be ready to place the cap—here a cap for female medical connector, in particular, for a needleless injection site—on the corresponding medical connector.

As described in connection with FIG. 3, embodiments of the present invention are equally applicable to caps for male connectors, so FIGS. 6-8 might have shown the user as having removed a cap for a male connector from an appropriately populated carrier 21, and being ready to place the male cap on a male medical connector.

FIGS. 6-8 show that the user may prepare a medical connector cap for use, with a single gesture that removes the medical connector cap from the carrier 21 and also removes the sealing tab 32 from the connector cap.

Although we have just shown how as part of the single gesture the sealing tab 32 may be removed from the connector cap, the sealing tab (and the tether 323 and tip 32) 1 may be configured so that when a user prepares the selected one of the caps for use, a user can choose to manipulate the cap in relation to the carrier (for example, by twisting it in place) so as to break the tether, and thereafter remove the cap from its corresponding hole, while leaving the cover portion of the sealing tab to sealingly cover the openable end of the cap. In this manner, a user may remove the cover portion at a desired time after removing the cap from its corresponding hole.

The embodiments herein described offer a number of advantages over prior art assemblies. First, the embodiments herein provide a mechanism, for mechanical mounting of the cap 31 in the carrier 21, that is distinct from the sealing mechanism that covers the openable end of the cap. By providing distinct mechanisms for mounting and for sealing, the embodiments herein provide much better protection to the caps from the effects of hard use in a hospital or other medical environment. Additionally, embodiments herein described provide a distinct cover for each cap, namely the cover portion 322 of the tab 32, whereas the prior art teaches the same sealing strip for all caps in the assembly. Whereas in the prior art any jostling of the assembly risks breaking the seal of any number of caps to the sealing strip, here any jostling of the assembly will be resisted by the friction fit of each cap in its corresponding hole in the carrier. Moreover, even if cap 31 were to move in relation to the carrier 21, still the cover portion 322 of the sealing tab can experience force only as applied through the tether 323 from the carrier 21 via tip 321. Because the tether 323 is flexible, the force experienced by the cover portion 322 is minimal, and thus the cover portion 322 provides a seal that is robust even when the assembly experience physically rugged forces. Moreover, as discussed, the tab can be configured so that a user can break the tether 323 and remove the cap from the carrier 21 while maintaining the cover portion 322 intact on the cap; in this way the cap can be transported after removal from the carrier 21 under conditions that avoid risk of contaminating the interior of the cap, whereas removing the cap from the assembly in the prior art necessarily exposes the interior of the cap to a risk of contamination.

The embodiments of the invention described above are intended to be merely exemplary; numerous variations and modifications will be apparent to those skilled in the art. All such variations and modifications are intended to be within the scope of the present invention as defined in any appended claims.

What is claimed is:

1. An assembly mounting medical connector caps for use, the assembly comprising:
   a carrier formed from a sheet of material, the carrier having an array of holes;
   a plurality of medical connector caps, each cap having (i) an openable end configured to cover a medical connector and (ii) a closed graspable end, wherein each cap is inserted into one of the holes of the array;
   a plurality of sealing tabs, wherein a distinct sealing tab includes a cover portion that sealingly covers the openable end of a corresponding one of the caps and includes an overhang portion that overhangs the openable end thereof, the overhang portion dimensioned to include a tether of sufficient length whereby a tip of the tether overlaps an adjacent portion of the carrier, the tip being affixed to the carrier, whereby the corresponding one of the caps is tethered to the carrier by said sealing tab;
   whereby a user can prepare a selected one of the caps for use by grasping its graspable end and both removing the selected cap from its corresponding hole and tearing away its openable end from the cover portion of the sealing tab, utilizing the tether to retain the sealing tab as affixed to the carrier.

2. An assembly according to claim 1, wherein the tether is configured whereby when the user prepares the selected one of the caps for use, the user can choose to manipulate the cap in relation to the carrier so as to break the tether and remove the cap from its corresponding hole, while leaving the cover portion of the sealing tab to sealingly cover the openable end of the cap, whereby the user may remove the cover portion at a desired time after removing the cap from its corresponding hole.

3. An assembly according to claim 1, wherein each of the holes into which one of the caps is inserted is sized to secure any of said caps therein with a friction fit, so as to mechanically stabilize such cap in relation to the carrier.

4. An assembly according to claim 2, wherein each of the holes into which one of the caps is inserted is sized to secure any of said caps therein with a friction fit, so as to mechanically stabilize such cap in relation to the carrier.

5. An assembly according to claim 1, wherein each of the caps includes a disinfectant disposed therein.

6. An assembly according to claim 1, wherein the sheet of material is flexible.

7. An assembly according to claim 6, wherein the sheet of material is a polymeric film.

8. An assembly according to claim 7, wherein the polymeric film is a polyolefin.

9. An assembly according to claim 8, wherein the polyolefin is selected from the group consisting of polyethylene and polypropylene.

10. An assembly according to claim 8, wherein the polyolefin is polyethylene.

11. An assembly according to claim 1, wherein the carrier includes at least one mounting hole.

12. An assembly according to claim 1, wherein the sealing tabs are made of metal foil.

13. An assembly according to claim 1, wherein the sealing tabs are made of a composite polymeric sheet with a metal foil layer.

* * * * *